United States Patent [19]
Kottenhahn et al.

[11] Patent Number: 5,744,611
[45] Date of Patent: Apr. 28, 1998

[54] PROCESS FOR THE REDUCTION OF AMINO ACIDS AND THE DERIVATIVES THEREOF

[75] Inventors: Matthias Kottenhahn; Karlheinz Drauz, both of Freigericht, Germany; Hans Hilpert, Reinach, Switzerland

[73] Assignees: Degussa Aktiengesellschaft, Frankfurt, Germany; Hoppman-La Rouche AG, Basel, Switzerland

[21] Appl. No.: 793,702
[22] PCT Filed: Aug. 17, 1996
[86] PCT No.: PCT/EP95/03281
§ 371 Date: Mar. 3, 1997
§ 102(e) Date: Mar. 3, 1997
[87] PCT Pub. No.: WO96/07634
PCT Pub. Date: Mar. 14, 1996

[30] Foreign Application Priority Data
Aug. 17, 1995 [DE] Germany ............... 44 31 529.5

[51] Int. Cl.$^6$ ........................... C07D 263/24
[52] U.S. Cl. .............. 548/232; 562/433; 562/445; 562/452
[58] Field of Search ............... 548/232; 562/433, 562/445, 452

[56] References Cited
FOREIGN PATENT DOCUMENTS
326934  8/1989  European Pat. Off.
4232505  3/1994  Germany.

OTHER PUBLICATIONS

Bull. Chem. Soc. Japan, vol. 57, pp. 2327–2328, Soai et al., 1984.
CA 101: 152278p Novel procedure . . . ester. Soai et al., 1984.

*Primary Examiner*—Joseph McKane
*Attorney, Agent, or Firm*—Cushman Darby & Cushman IP Group of Pillsbury Madison & Sutro LLP

[57] ABSTRACT

A process is disclosed for reducing amino acids and derivatives thereof Compounds of formula (I), in which n=0 or 1 and $R^1$, $R^2$, $R^3$, $R^4$, $R^5$ and $R^6$ have the meanings given in the description, are reduced to the corresponding amino alcohols of formula (II): the formula (I) compounds are converted in a first step, in at least one alcohol and with the addition of acid and heat to an ester, this process producing a reaction mixture containing the ester; the ester is converted in a second reaction step with alkali or alkaline earth borohydride to compounds of formula II. By specifying that the second step be carried out without isolating the ester from the reaction mixture and by using alkali or alkaline earth borohydrides which are not activated, the invention facilitates the production from amino acids and their derivatives of the correponding alcohols in a simple "single vessel" process, with high yields and in such a way as to preserve a given centre of chirality. Applications: synthesis components, preparation of optically active compounds splitting of racemic compounds.

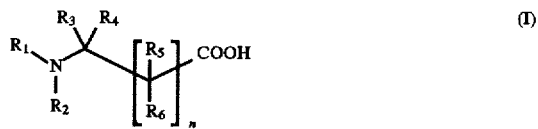

(I)

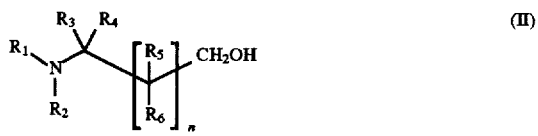

(II)

7 Claims, No Drawings

PROCESS FOR THE REDUCTION OF AMINO ACIDS AND THE DERIVATIVES THEREOF

CROSS-REFERENCE TO RELATED APPLICATIONS

This application claims priority from German application No. 4431529.5 filed Sep. 3, 1994 and PCT/EP95/03281 filed Aug. 17, 1995, the subject matter of which is hereby incorporated herein by reference.

FIELD OF THE INVENTION

The present invention relates to a process for the reduction of amino acids of the formula I

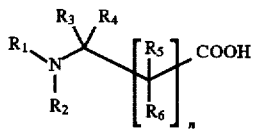

in which
n equals 0 or 1,
$R^1$, $R^2$, $R^4$, $R^5$, $R^6$ are mutually independently identical or different and mean H, aryl, alkyl or arylalkyl, wherein in the latter two cases the carbon chain may be substituted and/or interrupted by heteroatoms such as N, O or S or groups containing such atoms,
moreover
$R^1$ and $R^2$ may also mutually independently be identical or different and mean arylalkyloxycarbonyl, alkyloxycarbonyl or oxycarbonyl,
moreover
$R^3$, $R^4$, $R^5$ and $R^6$ may also mutually independently be identical or different and mean acylaminoalkyl or hydroxyl,
and
wherein
$R^3$, $R^4$, $R^5$ or $R^6$ may form a ring with $R^1$ or $R^2$, to yield the corresponding amino alcohols of the formula II

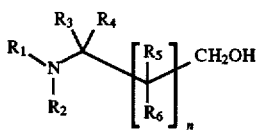

in which $R^1$ to $R^6$ and n have the meaning stated for the formula I,
in which process the compounds of the formula I are initially reacted in a first step in at least one linear or branched-chain alcohol having 1–5 C atoms with the addition of acid and with heating to yield an ester, wherein a reaction mixture containing the ester is obtained and the ester is reduced in a second step with alkali metal or alkaline earth metal borohydride to yield compounds of the formula II.

In the event that one of the residues $R^3$, $R^4$, $R^5$ or $R^6$ in the compounds of the type of formulae I, II forms a ring with one of the residues $R^1$ or $R^2$, it is understood that the name of both the residues involved in forming the ring will change in accordance with the rules of chemical nomenclature. Thus, if ring formation does occur, the corresponding residues $R^1$ to $R^6$ actually involved in forming the ring will be termed either alkylene or arylalkylene, wherein the carbon chain or ring thereof may be substituted by heteroatoms such as N, O and/or S or groups containing such atoms and/or interrupted by heteroatoms such as N, O and/or S, while $R^1$ and $R^2$ may, however, also be carbonyl, arylalkyleneoxycarbonyl, alkyleneoxycarbonyl or oxycarbonyl and $R^3$, $R^4$, $R^5$ or $R^6$ may be arylene, acylaminoalkylene or oxygen. As stated, these names should be used only for those residues actually attached to the ring. Otherwise, the generally stated names apply to those residues not involved in ring closure.

The amino alcohols obtainable by reducing amino acids or amino acid derivatives are versatile components for synthesis. In particular, the corresponding chiral compounds are important components, for example for preparing optically active compounds.

BACKGROUND OF THE INVENTION

A review of amino alcohols may be found in G. M. Coppola and H. F. Schuster, Asymmetric Synthesis, John Wiley & Sons, New York 1987; or in M. Nogradi, Stereoselective Synthesis, Verlag Chemie, Weinheim 1987.

The amino alcohols may thus be used to produce chiral catalysts, with which enantioselective cyclopropanations, reductions, hydrosilylations, Diels-Alder reactions and other reactions may be performed. This topic is reviewed in C. Bolm, Angew. Chem. 1991, 103, 556. The amino alcohols are frequently incorporated into important synthesis intermediates in order to induce the formation of centres of asymmetry in subsequent reactions by the action of steric or electronic influences, wherein the degrees of enantio- or diastereoselectivity are frequently extraordinarily high. Examples which may be mentioned are 4-substituted oxazolidin-2-ones (J. R. Gage, D. A. Evans, Org. Synth. 1989, 68, 77 and the literature cited therein) and bicyclic lactams (D. Romo, A. I. Meyers, Tetrahedron 1991, 47, 9503).

Amino alcohols may also be integrated into peptide isosteres, wherein products having elevated physiological activity may be obtained, for example enkephalin analogues having a stronger and longer lasting analgesic action (Y. Kiso, M. Yamaguchi, T. Akita, H. Moritoki, M. Takei, H. Nakamura, Naturwissenschaften 1981, 68, 210; J. Pless, W. Bauer, F. Cardinaux, A. Closse, D. Hauser, R. Huguenin, D. Roemer, H. H. Buescher, R. C. Hill, Helv. Chim. Acta 1919[sic], 62, 398) or also HIV protease inhibitors (for example T. F. Tam, J. Carriere, I. D. MacDonald, A. L. Castehano, D. H. Pliura, N. J. Dewdney, E. M. Thomas, C. Bach, J. Barnett, H. Chan, A. Krantz, J. Med. Chem. 1992, 35(7), 1318). Amino alcohols are also suitable as a C-terminal protective group in peptide synthesis (C. Kashima, K. Harada, Y. Fujiioka, T. Maruyama, Y. Omote, J. Chem. Soc. Perkin Trans. 1 1988, 535).

Chiral amino alcohols have been used to resolve racemates, either by fractionally crystallising diastereomeric salts of N-alkylamino alcohols (M. Tukamoto, T. Sawayama, Dainippon Pharmaceutical Co., EP 0 105 696 A1, 18.04.1984, F. Horiuchi, M. Matsui, Agric. Biol. Chem. 1973, 37, 1713) or by chromatographically separating diastereomeric addition compounds (K. Ogura, M. Ishida, H. Tomori, M. Fujita, Bull. Chem. Soc. Jpn. 1989, 62, 3531).

Finally, 1,3,2-oxazophospholidine-2-sulphides derived from amino alcohols have been found to have insecticidal activity (S. Wu, R. Takeya, M. Eto, C. Tomizawa, J. Pesticide Sci. 1987, 12, 221).

There are various methods for the production of optically active amino alcohols. They may be obtained, for example, by resolving racemates, which may be achieved either by conventional fractional crystallisation of diastereomeric salts as in the case of (S)-2-aminobutanol, the precursor of the tuberculostatic ethambutol (F. Lanzendörfer, G. Fritz, H.

Siegel, BASF AG, DE 35 17 108 A1, 13.11.1986 and the literature cited therein), or by enzymatic cleavage of suitable derivatives (F. Francalani, P. Cesti, W. Cabri, D. Bianchi, T. Martinego, M. Foa, *J. Org. Chem.* 1987, 52, 5079 and the literature cited therein, H. S. Bevinakatti, R. V. Nevadklar, *Tetrahedron: Asym.* 1990, 1, 583).

Reductive methods differ fundamentally from the above. Optically active amino alcohols were first obtained by reducing optically active amino acid esters, although with considerable racemisation (P. Karrer, W. Karrer, H. Thomann, E. Horlacher, W. Mäder, Helv. Chim. Acta 1921, 4, 76). It subsequently proved possible also to perform this reaction using lithium aluminium hydride (P. Karrer, P. Portmann, M. Suter, *Helv. Chim. Acta* 1948, 31, 1617; P. S. Verkateswaran, T. J. Bardo, *J. Org. Chem.* 1967, 32, 1256), sodium borohydride (H. Seki, K. Koga, H. Matsuo, S. Ohki, I. Matsuo, S. Yamada, *Chem. Pharm. Bull.* 1965, 13, 995), lithium borohydride (Barton & Ollis, *Comprehensive organic chemistry*, volume 3 (1979), bottom of page 773) or sodium borohydride with methanol as an activator (*Bull. Chem. Soc. Jpn.* 57 (1984), pp. 2327 et seq. and *Chem. Abstr.* 101 (1984), 152278p), wherein it could be demonstrated that these and other hydride reductions proceeded virtually without racemisation (G. S. Poindexter, A. I. Meyers, *Tetrahedron Lett.* 1977, 3527). However, a disadvantage of methanol "activation" is inter alia mixing with solvents because it renders large-scale industrial reprocessing of the solvent more difficult. Due to the time-consuming two-stage process with intermediate isolation of the ester and the elevated hydride excesses when alkali metal borohydrides are used, reduction of the free optically active amino acids with lithium aluminium hydride has become established as the standard process (D. A. Dickmann, A. I. Meyers, G. A. Smith, R. E. Gawley, *Organic Syntheses Coll.*, volume VII, p. 539, John Wiley & Sons, New York 1990). It is also possible to use a borane/dimethyl sulphide complex with activation by boron trifluoride etherate (J. R. Gage, D. A. Evans, *Org. Synth.* 1989, 68, 77; G. A. Smith, R. E. Gawley, *Org. Synth.* 1985, 63, 136).

It has recently been possible to demonstrate that, with suitable activation, lithium borohydride (with trimethylchlorosilane: R. Dharanipragada, A. Alarcon, V. J. Hruby, *Org. Prep. Proc. Int.* 1991, 23, 396; with boron trifluoride etherate: W. H. J. Boesten, C. H. M. Schepers, M. J. A. Roberts (Stamicarbon B.V.) EP 0 322 982 A2, 05.07.1989) or the combination NaBH$_4$/H$_2$SO$_4$ (A. Abiko, S. Masamune, *Tetrahedron Lett.* 33(28), 1992, 5517) may also be used for the direct reduction of amino acids.

However, all the stated methods have disadvantages which have hitherto prevented their use on a larger scale. The two-stage reactions passing via the isolated ester intermediate are, from the outset, too time-consuming and moreover costly due to the elevated hydride excesses. While reductions with lithium aluminium hydride may indeed be performed quickly and efficiently on a laboratory scale, particular safety precautions are required on the industrial scale due to the elevated flammability of the hydride. The reagent is moreover uneconomic due to its high price. Use of a borane/dimethyl sulphide adduct is associated with a considerable odour nuisance. In those processes using boron trifluoride etherate as the activator, this reagent is used in molar quantities, so causing increasing problems with the disposal of the fluoride-containing wastes. The addition of alkylhalosilanes to activate the alkali metal borohydride results in the formation of silanes or siloxanes which can be put to no further use. It has hitherto been possible to use the combination NaBH$_4$/H$_2$SO$_4$ only with ethers as the solvent, wherein these are either expensive or questionable on safety grounds. Considerable molar excesses of NaBH$_4$ must additionally be used. Various NaBH$_4$-based reduction methods for free or N-protected amino acids, inter alia the NaBH$_4$-I$_2$ system, are known from *Tetrahedron Lett.* 33, 5517–8, 1992 and *J. Org. Chem.* 1993, 58, 3568. Only the carboxylic acid is reduced in these methods, but, despite the use of simple amino acids (for example L-valine), yields are very low for some systems and furthermore the production of relatively large quantities of iodine waste is associated with high disposal and recycling costs.

SUMMARY OF THE INVENTION

In view of the disadvantages of the prior art, the object of the invention is to provide a process for the reduction of amino acids or the derivatives thereof in order to prepare the corresponding amino alcohols, in which process it should be possible to perform the reduction under mild conditions and while retaining any chiral centers. It should be possible to perform the reaction using low cost reagents which may easily and safely be handled even on an industrial scale, wherein, on completion of the reaction, it should be possible to work up the product simply and to dispose of the residual substances straightforwardly.

will become apparent to those skilled in the art upon reading the specification and appended claims.

Due to the esterification of the amino acid or the amino acid derivative and subsequent reduction with non-activated alkali metal or alkaline earth metal borohydrides without intermediate isolation of the esters, it is possible to produce the corresponding alcohols from amino acids or amino acid derivatives in a simple "single vessel" process at high yield while retaining any chiral centers possibly present.

While reducing a-amino acid derivatives to the α-amino alcohols via an amino acid ester intermediate with sodium borohydride is indeed known in principle (H. Seki, K. Koga, H. Matsuo, S. Ohki, I. Matsua, S. Yamada, *Chem. Pharm. Bull.* 13 (8), 995, 1965; S. Mandal, B. Achari, S. Chattopadhyay, *Tetrahedron Lett.* 33 (12), 1992, 1647), this process, involving prior isolation and drying of the esters or salts thereof, possible subsequent liberation from the salts with alkali hydroxide solution and subsequent reduction with 4–5 mol equivalents of NaBH$_4$ was complex, time-consuming and costly.

In contrast, the process of the invention avoids the disadvantageous isolation of the intermediate product.

The process according to the invention may be subdivided into two theoretical steps or stages. The first stage involves esterification of the amino acids or the amino acid derivatives, while the second stage comprises the actual reduction of the ester intermediates. It is, however, an essential feature of the invention and explicitly stated that when the invention is performed both stages or steps are performed in succession without the product of the first reaction stage being isolated, i.e. without the intermediate being isolated from the resultant reaction mixture.

It has now been found that, despite dispensing with isolation of the ester produced as the intermediate of the process according to the invention on completion of the first reaction step, the entire reaction may be performed at elevated yield if, in order to reduce the intermediate, only alkali metal or alkaline earth metal borohydride, without the addition a reducing agent activating substance, is added to the reaction mixture arising from the first step. This result was not to be expected as the use of "clean" intermediates or activation of the borohydride had hitherto always appeared essential in order to achieve a satisfactory yield.

DETAILED DESCRIPTION OF THE INVENTION

Esterification as the first stage of the process according to the invention is performed using processes known from the literature (Houben Weyl, volume 15) by suspending or dissolving the amino acid to be reduced or the corresponding amino acid derivative in a $C_1$–$C_5$ alcohol with the addition of acid and heating the reaction solution, optionally up to the boiling point of the reaction mixture.

Alcohols which may successfully be used for the purposes of the invention include, by way of non-limiting example, linear alcohols such as methanol, ethanol, propanol, butanol and branched-chain alcohols such as isopropanol. Methanol and ethanol are preferably used as the alcohols.

Acids which may successfully be added are, for example, HCl, $H_2SO_4$, 4-toluenesulphonic acid, methanesulphonic acid, benzenesulphonic acid, polysiloxanesulphonic acids as well as mixtures of two or more of the above-stated components. Of the listed acids, HCl, $H_2SO_4$ or para-toluenesulphonic acid or mixtures thereof are preferred.

The acids or acid mixtures are generally used in a quantity of 0.05–3 mol equivalents, preferably 0.1–1.5 mol equivalents, relative to the amino acid to be reduced or the amino acid derivative to be reduced.

If the amino acid to be reduced or the amino acid derivative to be reduced is an amino acid which is unprotected on the nitrogen of the amino group, one equivalent of acid is required to neutralise the amino function in addition to the quantity of acid required for esterification catalysis.

Once the first or esterification step is complete, it is possible according to the invention in principle to continue directly with the second or reduction step, i.e. with the reduction of the intermediately formed ester product. It is, however, possible and preferred in the context of the invention, optionally to concentrate the intermediate product from the first stage, which may be in the form of a solution, by removing excess liquid constituents from the reaction mixture, for example by evaporation or distillation. The aim of this concentration is in particular to complete esterification, to recover solvent and to restrict the volume of the reaction mixture in the reduction stage.

It is moreover also possible to neutralise any acid excess present in the solution of the intermediate product optionally by adding bases. Any basic substances familiar to the person skilled in the art may in principle be used for this purpose, but alkalies are preferably used, such as for example sodium hydroxide, sodium hydroxide solution, potassium hydroxide, potassium hydroxide solution, sodium alkoxide, potassium alkoxide, sodium carbonate, sodium hydrogen carbonate, potassium carbonate or potassium hydrogen carbonate. Thanks to this measure it is in particular advantageously possible optionally further to reduce the hydride excess to be used in the subsequent reduction stage.

For the purposes of the second reaction step of the invention, 1–<5 mol equivalents of alkali metal or alkaline earth metal borohydride are added as the reducing agent to the reaction mixture, which has optionally been treated as described above, arising from the first step or esterification step.

According to the invention, reducing agents which may successfully be used include inter alia $NaBH_4$, $LiBH_4$, $KBH_4$, $Ca(BH_4)_2$. Particularly preferred alkali metal or alkaline earth metal borohydrides are: $NaBH_4$ or $LiBH_4$.

In the light of hitherto prevailing opinion, it must be considered entirely surprising that it was possible in a preferred modification of the process according to the invention to reduce the quantity of alkali metal or alkaline earth metal borohydride to be added for reduction below the quantity hitherto used to a molar excess of approximately 5 times, relative to the ester to be reduced, without having to accept any reduction in yield.

In a further preferred embodiment, the reducing agent is used in a molar excess of only 1.1 to 3 times, relative to the ester produced as an intermediate product. A quantity of alkali metal or alkaline earth metal borohydride amounting to a molar excess of only between 1.2 and 2 times is particularly preferably used.

The temperature for the performance of the actual reduction step is not in principle critical, but it should be between −20° C. and the boiling temperature of the solvent. If a temperature of below −20 C. is used, the rate of the reduction reaction may be too low.

The reduction process of the invention may be applied to a wide range of compounds. Amino acids or amino acid derivatives of the formula I where n=0 thus in particular include α-amino acids or α-amino acid derivatives of the formula III

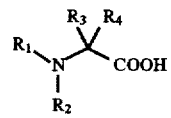

III or, where n=1, β-amino acids or the derivatives thereof of the formula IV

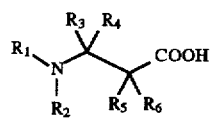

IV in which $R^1$ to $R^6$ in each case have the meaning stated for the formula I and are also subject to the same conditions stated at that point, in particular also in relation to an optionally present ring between $R^1$ or $R^2$ and $R^3$, $R^4$, $R^5$ or $R^6$.

The compounds reduced according to the invention are particularly advantageously those in which there is ring closure between $R^2$=carbonyl and $R^5$=oxygen.

In these cases it is furthermore preferred that $R^1$=$R^6$=$R^4$=H and the compounds to be reduced comply with the general formula V

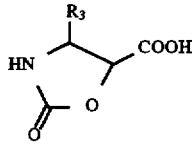

V in which $R^3$ may have the meaning stated for the formula I.

Particularly advantageous features of the process of the invention are the reduction in isolation steps, the use of low cost reagents and solvents and the small excess of borohydride.

The amino alcohols obtainable according to the invention may be worked up using known processes, wherein, once the organic solvent has been distilled off, excess reducing agent and stable boron-amine/alkoxide complexes are first decomposed by the careful addition of water or aqueous acid. An optionally crystalline reaction product is then separated or directly, or once a basic pH has been established, extracted from the aqueous phase of the reaction product using a suitable organic solvent, optionally after further derivativisation on one of the free functional groups, and, if necessary, further purified by distillation, crystallisation or chromatography.

The following Examples further illustrate the process:

EXAMPLE 1

Z-L-phenylalaninol 9 g (30 mmol) of Z-phenylalanine were dissolved in 100 ml of ethanol and, after the addition of 0.32 ml of concentrated $H_2SO_4$ (6 mmol), refluxed for 2 hours. After this time, HPLC revealed a conversion of approximately 98% to the Z-phenylalanine ethyl ester. The solution was cooled to room temperature, combined with 0.4 g of NaOH ground in a mortar (10 mmol) and added dropwise within 15 minutes to a suspension of 1.57 g (42 mmol) of $NaBH_4$ in 100 ml of ethanol. On completion of the reaction, the alcohol was removed by distillation and the residue redissolved in 100 ml of water. A pH value of 3 was established by adding concentrated hydrochloric acid. On completion of foaming, a pH of 12 was established with NaOH and the mixture extracted once with hot toluene. The toluene phase was concentrated and then left to stand for some hours at 4° C. The precipitated solid was separated using a vacuum filter, washed with hexane and dried under a vacuum.

Yield: 6.5 g=72% of theoretical (the aqueous phase still contains 10–15% of the theoretical product, which may be isolated by another extraction with toluene). NMR: corresponds to reference Purity (HPLC): >99%

EXAMPLE 2

(4S,5S)-4-benzyl-5-hydroxymethyl-oxazolidin-2-one 22.1 g (100 mmol) of (4S,5S)-4-benzyl-oxazolidin-2-one-5-carboxylic acid were dissolved in 120 ml of ethanol. 1.2 ml of concentrated sulphuric acid (11 mmol) were added and the mixture refluxed for 2 hours. 90 ml of ethanol were then removed by distillation. This solution was then added dropwise within 30 minutes to a suspension of 5.3 g (140 mmol) of $NaBH_4$ in 40 ml of ethanol. Once addition was complete, stirring was continued for 3 hours. 100 ml of water were cautiously added to the colourless suspension and a pH value of 7 was established with concentrated HCl. After 2 hours' stirring at room temperature, the temperature was reduced to 0° C. for a further 2 hours. The solid was filtered out and washed with a little iced water. The product was then dried under a vacuum at 45° C.

Yield: 18.68 g (90.1% of theoretical) of colourless solid NMR: corresponds to reference Purity (HPLC): 99%

EXAMPLE 3

Z-L-threoninol 50.65 g (200 mmol) of Z-L-threonine were dissolved in 200 ml of ethanol and, after the addition of 2.2 mmol of concentrated $H_2SO_4$ (40 mmol), refluxed for 2.5 hours. 100 ml of toluene were added and 250 ml removed by distillation. 200 ml of ethanol were then added, the mixture cooled to room temperature and added dropwise within 75 minutes to a suspension of 12.5 g (330 mmol) of $NaBH_4$ in 200 ml of ethanol. After a reaction time of 1 hour, the mixture was combined with 100 ml of water and the pH adjusted to 7 with concentrated HCl. The mixture was then largely evaporated and the residue redissolved with 400 ml of water. The aqueous phase was extracted once with 250 ml of ethyl acetate and twice with 100 ml portions of ethyl acetate. Once the ethyl acetate had been distilled off, 47.3 g of oil were obtained which had a product content of 88%.

Yield: 47.3 g of (88%) oil NMR: corresponds to reference, contains ethyl acetate Purity, HPLC: >98%

EXAMPLE 4

L-valinol 58.6 g (500 mmol) of L-valine were suspended in 500 ml of ethanol and, after the addition of 100 g of concentrated $H_2SO_4$ (1 mol), refluxed for 5 hours. 40 ml of ethanol were added and the mixture cooled to room temperature. 120 ml of the solution (one fifth) were then added dropwise within 75 minutes to a suspension of 5.7 g (150 mmol) of $NaBH_4$ in 100 ml of ethanol. After a reaction time of 12 hours, the ethanol was removed by vacuum distillation, the residue combined with 100 ml of water and a pH value of 12 established with 20% NaOH. The aqueous phase was extracted twice with 150 ml portions of methylene chloride, the extracts dried over sodium sulphate and largely evaporated under a vacuum. A colourless, readily mobile liquid was obtained.

Yield: 11.3 g of colourless oil Titration: 66.4%=72.8% of theoretical Thin layer chromatography: corresponds to reference, uniform

EXAMPLE 5

(4S,5S)-4-benzyl-5-hydroxymethyl-oxazolidin-2-one 1.1 g (5 mmol) of (4S,5S)-4-benzyl-oxazolidin-2-one-5-carboxylic acid were dissolved in 15 ml of ethanol. 0.03 ml of sulphuric acid were added and the mixture refluxed for 4 hours. After cooling, 0.04 g of NaOH were added and the mixture concentrated under a vacuum to 2 g. 4 ml of ethanol were then added and 0.25 g of $NaBH_4$ was added in small portions. Once addition was complete and stirring had been continued for 0.5 hour, the educt was already completely converted. 4 ml of water were added, the mixture neutralised to pH 7 with 1.2 ml of 10% HCl and, after cooling, cooled to 0° C. The solid was separated using a vacuum filter and, due to the small batch size, washed with a disproportionately large quantity of water. The yield after isolation was 0.66 g=63.7%, wherein approximately 0.2 g=20% of theoretical still remained in the mother liquor and washing water. Diastereomer purity was S,S:R,S=98.75:1.

Further embodiments and advantages of the invention are stated in the following claims.

We claim:

1. Process for the reduction of amino acids of the formula I

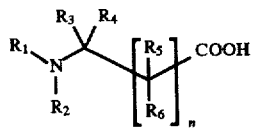

in which n equals 0 or 1, $R^1$, $R^2$, $R^3$, $R^4$, $R^5$, $R^6$ are mutually independently identical or different and are H, aryl, alkyl or arylalkyl, wherein in the latter two groups the carbon chain may be substituted and/or interrupted by heteroatoms or $R^1$ and $R^2$ are mutually independently identical or different and mean arylalkyloxycarbonyl, alkyloxycarbonyl or oxycarbonyl, or $R^1$, $R^4$, $R^5$ and $R^6$ are mutually independently identical or different and are acylaminoalkyl or hydroxyl, and wherein $R^3$, $R^4$, $R^5$ or $R^6$ may form a ring with $R^1$ or $R^2$, to yield the corresponding amino alcohols of the formula II

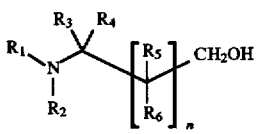

in which $R^1$ to $R^6$ and n have the meaning stated for the formula I, in which process the compounds of the formula I are initially reacted in a first step in at least one linear or branched-chain alcohol having 1–5 C atoms with the addition of acid and with heating to yield an ester, wherein a reaction mixture containing the ester is obtained and the ester is reduced in a second step with alkali metal or alkaline earth metal borohydride to yield compounds of the formula II, wherein the second step is performed without isolating the ester from the reaction mixture and the alkali metal or alkaline earth metal borohydrides are used without the addition of a reducing agent activating substance to the reaction mixture produced in the first step.

2. Process according to claim 1, wherein the alkali metal or alkaline earth metal borohydride is used in a 1 to less than 5 times molar excess, relative to the compound of the formula I.

3. Process according to claim 1, wherein the acid in the first step is HCl, sulphuric acid or para-toluenesulphonic acid.

4. Process according to claim 1, wherein the alkali metal or alkaline earth metal borohydride is sodium borohydride, lithium borohydride, potassium borohydride or calcium borohydride.

5. Process according to claim 1, wherein a base is added to the reaction mixture after the first step and before the second step.

6. Process according to claim 1, wherein reduction with borohydride is performed in a temperature range from −20° C. to the boiling temperature of reduction mixture.

7. Process according to claim 1 for the reduction of amino acids of formula I wherein the amino acid has the formula V

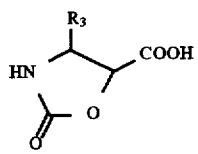

in which $R^3$ has the meaning as defined for formula I.

* * * * *

UNITED STATES PATENT AND TRADEMARK OFFICE
CERTIFICATE OF CORRECTION

PATENT NO. : 5,744,611
DATED : April 28, 1998
INVENTOR(S) : KOTTENHAHN, et al.

It is certified that error appears in the above-identified patent and that said Letters Patent is hereby corrected as shown below:

On the title page, item [73], change:

"Hoppman-La Rouche AG" to
--F. Hoffmann-La Roche AG--

Signed and Sealed this

Twenty-second Day of June, 1999

Attest:

Attesting Officer

Q. TODD DICKINSON

Acting Commissioner of Patents and Trademarks